United States Patent [19] [11] 3,957,818
Carson [45] May 18, 1976

[54] PREPARATION OF PYRROLE-2-ACETIC ACID DERIVATIVES
[75] Inventor: John Robert Carson, Norristown, Pa.
[73] Assignee: McNeil Laboratories, Incorporated, Fort Washington, Pa.
[22] Filed: Nov. 7, 1974
[21] Appl. No.: 521,703

Related U.S. Application Data
[63] Continuation-in-part of Ser. No. 309,410, Nov. 24, 1972, abandoned.

[52] U.S. Cl. .................. 260/326.2; 260/326.46; 260/326.62; 260/326.82
[51] Int. Cl.² ..................................... C07D 207/32
[58] Field of Search .................. 260/326.2, 326.62

[56] References Cited
UNITED STATES PATENTS
3,544,589 12/1970 Orth et al. .................. 260/326.62

Primary Examiner—R. Gallagher
Attorney, Agent, or Firm—Salvatore R. Conte

[57] ABSTRACT

Catalytic dehydrogenation of $\Delta$-2,$\alpha$-pyrrolidenemalonates and $\Delta$-2,$\alpha$-pyrrolidenemalononitriles yields pyrrole-2-acetates and pyrrole-2-acetonitriles, respectively. Subsequent hydrolysis of the latter affords pyrrole-2-acetic acids.

18 Claims, No Drawings

PREPARATION OF PYRROLE-2-ACETIC ACID DERIVATIVES

RELATED APPLICATION

This is a continuation-in-part application of my co-pending application Ser. No. 309,410, filed Nov. 24, 1972, now abandoned.

BACKGROUND OF THE INVENTION

5-Aroyl-pyrrole-2-acetic acid derivatives, such as acids, esters and nitriles, have been reported in the literature as being useful anti-inflammatory agents (e.g., see Belgian Pat. No. 762,060). The subject invention offers a convenient method for making pyrrole-2-acetic acid esters and acetonitriles which are useful as starting materials in the production of such anti-inflammatory agents. For example, said esters and nitriles may be readily acylated in the 5-position to provide the appropriate 5-aroyl function of such anti-inflammatory agents. In addition, said esters and nitriles may be readily hydrolyzed to the corresponding acid state, which acids may in turn be esterified by conventional esterification procedures and then acylated in the 5-position.

DESCRIPTION OF THE PREFERRED EMBODIMENTS

This invention relates to a novel process of preparing pyrrole-2-acetic acid derivatives of the formula:

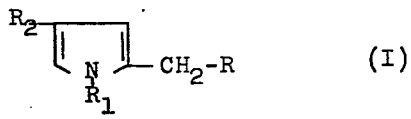

wherein R is a member selected from the group consisting of COO(loweralkyl) and CN; $R_1$ is a member selected from the group consisting of hydrogen and loweralkyl, preferably methyl; and $R_2$ is a member selected from the group consisting of hydrogen and methyl.

As used herein, "loweralkyl" refers to straight or branch chained alkyls having from 1 to 6 carbons, for example, methyl, ethyl, propyl, isopropyl, butyl, tert-butyl, pentyl, hexyl and the like.

According to the instant process, an appropriate pyrrolidenemalonic acid derivative of formula (II), wherein $R_1$ and $R_2$ are as previously defined and X and Y are each a member selected from the group consisting of COO(loweralkyl) and CN, is catalytically dehydrogenated to yield the corresponding pyrroleacetic acid derivatives of formulas (III-a) and (III-b):

The catalytic dehydrogenation step may be effected in the liquid or vapor phase over a catalyst suitable for dehydrogenation reactions. Typical such catalysts are the noble metals such as palladium, platinum, rhodium, rhenium, ruthenium, iridium and the like, and some transition metals that are also suitable for dehydrogenation purposes such as nickel, chromium and cobalt. The preferred dehydrogenation catalysts are palladium, platinum and rhodium. Depending on the particular metal, the catalyst may be employed in the form of the free metal or in the form of an oxide or salt, e.g., the sulfide or halide, or in the form of a soluble complex, e.g., $Rh(\phi_3P)_3Cl$. The catalyst may be supported, e.g., on carbon, $Al_2O_3$, $CaCO_3$, $BaCO_3$, $SiO_2$ and the like, or unsupported. Palladium deposited on charcoal is the preferred catalyst herein, particularly for liquid-phase dehydrogenations. The reaction may be performed in a pressure vessel or in a high boiling solvent. Suitable inert organic solvents that are employed in dehydrogenation reactions may be utilized, such as, for example, an aromatic hydrocarbon such as benzene, toluene, xylene and the like; an ether such as dioxane, tetrahydrofuran and the like; or a high boiling solvent, such as p-cymene, naphthalene, α-methylnaphthalene, mesitylene, phenanthrene, decalin, quinoline, nitrobenzene, oleic esters and the like, depending upon the reaction temperature desired. High temperatures of 150°-450°C are generally required, with 180°-280°C preferred. In liquid-phase dehydrogenations, provision is made for removing the hydrogen that is eliminated from the starting material (II) in order to drive the dehydrogenation reaction to completion, such as by sweeping it out with an inert gas or by use of a hydrogen-acceptor, such as, for example, an unsaturated hydrocarbon, e.g., ethylene, or an unsaturated solvent, e.g., an oleic ester, or a compound capable or reduction, e.g., nitrobenzene.

It is evident in the catalytic dehydrogenation step that, when X and Y of formula (II) are the same function, then the resultant (III-a) and (III-b) will be identical, thereby giving rise to a single dehydrogenated product. When X and Y of formula (II) are different functions, for example, a mixed di-ester or a nitrile-ester, then the resultant (III-a) and (III-b) will be different. Subsequent hydrolysis of the dehydrogenated products (III-a) and (III-b) affords the corresponding pyrrole-2-acetic acids of formula (IV). When (III-a) and (III-b) are different, the two need not be separated, for purposes of convenience, but may be simply hydrolyzed together to obtain the pyrrole-2-acetic acid (IV). Esterification of (IV), for example, by standard treatment with an appropriate lower alkanol, affords the pyrrole-2-acetates of formula (I).

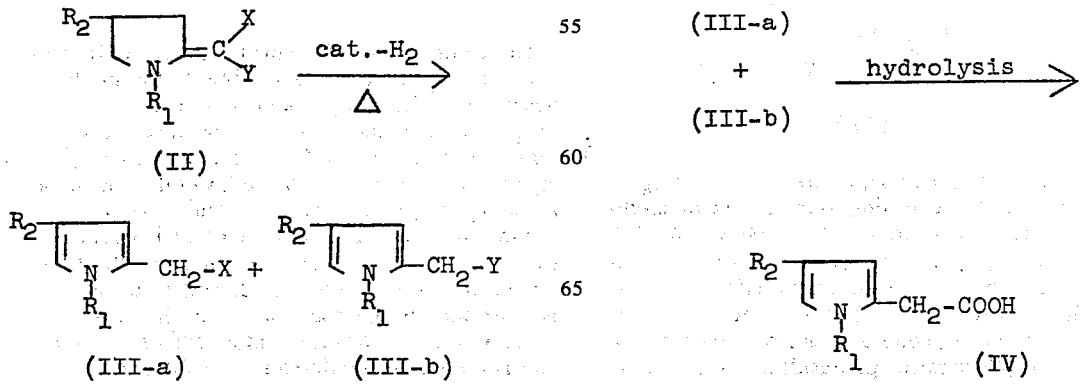

esterification
⟶
(lower alkanol)

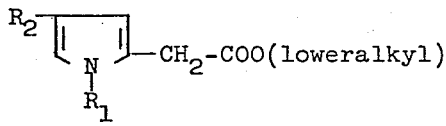
$R_2$, N-$R_1$, —$CH_2$—COO(loweralkyl)

With regard to the hydrolysis step, standard nitrile-to-acid and ester-to-acid hydrolysis procedures are employed, for example, alkaline hydrolysis in an appropriate alkanol, in order to transform the respective nitrile and ester functions to the corresponding acid form.

The starting materials of formula (II), several of which are known, may be prepared according to procedures described in the literature. For example, the compounds of formula (II), wherein $R_1$ is hydrogen, are obtained by the thermal condensation of an appropriate O-alkyl butyrolactim, e.g., the O-methyl butyrolactim of formula (V), with an appropriate malonitrile, diloweralkyl malonate or loweralkyl cyanoacetate of formula (VI), wherein X and Y are each a member selected from the group consisting of COO(loweralkyl) and CN, according to the methodology described in Yamada and Matsui, J. Agr. Biol, Chem. 34, 724 (1970) and by Bohlmann and Ottawa, C.A., 52, 10800e (1958). The resultant product (II) is isolated according to standard fractional distillation techniques. This procedure is demonstrated more fully in Example I hereafter and by the following schematic diagram:

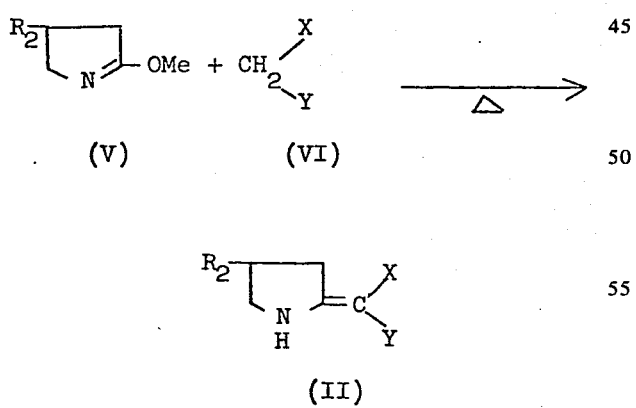

The di-esters of formula (II), wherein $R_1$ is hydrogen, may also be obtained according to the following methodology reported by Roth et al. in Helv. 54, 720 (1971): an appropriate 4-$R_2$-pyrrolidin-2-one of formula (VII) is converted to the corresponding 4-$R_2$-pyrrolidin-2-thione of formula (VIII) by standard oxo-to-thio transformation procedures, e.g., by treatment of the former with phosphorus pentasulfide in a suitable solvent, e.g., an aromatic hydrocarbon such as benzene, toluene, xylene and the like. Elevated temperatures may be employed to enhance the rate of reaction. The thus-obtained thione (VIII) is then reacted with an appropriate di-loweralkyl halomalonate of formula (IX) preferably the bromomalonate, in a suitable organic solvent, e.g., dichloromethane, chloroform and the like. The resultant thioimidate hydrohalide intermediate is then treated with a weak inorganic or organic base, such as an alkali metal carbonate or bicarbonate, a trialkylamine, pyridine and the like, and the released elemental sulfur from (VIII) removed, to yield the desired di-ester. This procedure is more fully demonstrated in Examples VIII and IX hereafter and by the following schematic diagram:

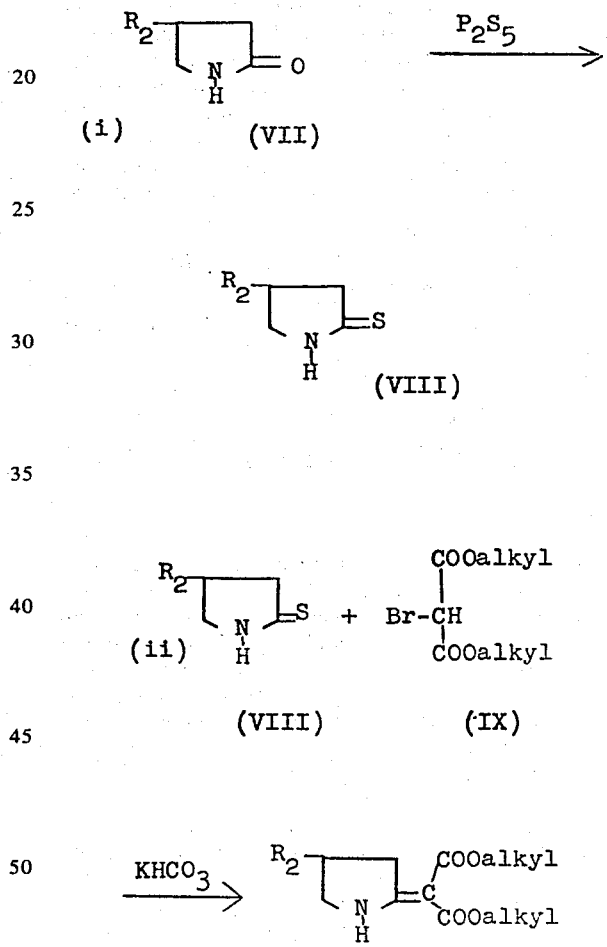

The compounds of formula (II), wherein $R_1$ is lower-alkyl, may be prepared according to the methodology described by H. Bredereck et al., Ber. 94, 2278 (1961). In general, an appropriate 1-loweralkyl-4-$R_2$-pyrrolidin-2-one of formula (X) is treated with phosgene and an appropriate malonitrile, diloweralkyl malonate or lower-alkyl cyanoacetate of formula (VI) in a suitable organic solvent, e.g., an aromatic hydrocarbon, in the presence of a base, such as, for example, a tertiary amine, which base acts as a scavenger for the HCl that is liberated during the course of the reaction. This procedure is demonstrated more fully in Example (V) and is schematically illustrated as follows:

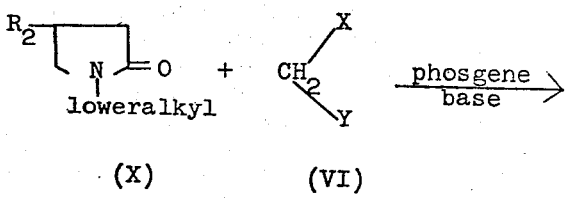

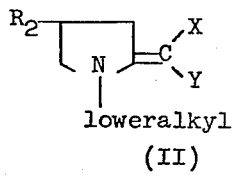

The preparation of 1,4-dimethyl-pyrrolidin-2-one is discussed by Fable & Korte in Chem. Ber. 98, 1928 (1965). The preparation of other 1-loweralkyl-4-$R_2$-pyrrolidin-2-ones of formula (X) can be accomplished according to the methodology of this reference by substituting an appropriate loweralkyl primary amine in the reaction with methallyl chloride. This process is further discussed in German Pat. No. 1,227,450 issued to these authors.

The compounds of formula (I) are useful precursors for making the 5-aroyl-pyrrole-2-acetic acid derivatives useful as anti-inflammatory agents described in my copending application, Ser. No. 5,958, filed Jan. 26, 1970, and now U.S. Pat. No. 3,752,826 entitled "Aroyl-Substituted Pyrroles". The subject compounds (I) are also useful as starting materials in the production of phenothiazine derivatives which are useful in medicine as antihistamines, spasmolytics and local anesthetics (see U.S. Pat. No. 3,544,589).

In view of the fact that the pyrrole-2-acetic acids of formula (IV) are also useful precursors for making the aforementioned 5-aroyl-pyrrole-2-acetic acid derivatives, the two-step method (catalytic dehydrogenation followed by hydrolysis) described hereinabove for making (IV) constitutes an additional feature of this invention.

The following examples are intended to illustrate, but not to limit, the scope of the present invention. Unless otherwise stated, all parts are by weight.

EXAMPLE I

Dimethyl-Δ-2,α-pyrrolidenemalonate

A mixture of 56.7 g (0.43 mole) of dimethyl malonate and 42.5 g (0.43 mole) of O-methyl butyrolactim [See Peterson & Tietze, Ber. 90, 920 (1957)] is heated. Volatile materials are distilled until the temperature of the reaction mixture reaches 126°C. The mixture is then heated under reflux for 2 days. The mixture is then distilled under reduced pressure through a Vigreaux column. Fractions are obtained as follows: 19.7g, b.p. 73°C, 15 mm (dimethyl malonate; 7 g, b.p. 32°–120°C, 0.3 mm (mixture); 19.2 g, b.p. 132°C, 0.3 mm (dimethyl Δ-2,α-pyrrolidenemalonate). The last fraction crystallizes and the product is recrystallized from ethyl acetate-hexane to give about 14.0 g of dimethyl Δ-2,α-pyrrolidenemalonate colorless crystals, m.p. 68°–70°C.

EXAMPLE II

Methyl pyrrole-2-acetate

A mixture of 5.0 g of dimethyl-Δ-2,α-pyrrolidenemalonate. 5.0 g, of 10% palladium on carbon, and 50 g. of phenanthrene is heated at 180°C under carbon dioxide for 18 hours. The mixture is then dissolved in $CHCl_3$, the palladium catalyst is removed by filtration and the $CHCl_3$ evaporated in vacuo. The residue is distilled through a Vigreaux column to give 0.5 g of methyl pyrrole-2-acetate as a colorless oil, b.p. 113°–120°C at 10 mm/Hg.

EXAMPLE III

1-Methylpyrrole-2-acetonitrile

A mixture of 5.0 g of 1-methyl-Δ-2,α-pyrrolidenemalononitrile [see H. Bredereck et al., Ber. 94, 2278 (1961)], 25 g of 10% palladium on carbon and 105 ml of ethyl oleate is heated at 280°C under nitrogen for 18 hours. The mixture is then dissolved in $CHCl_3$, the palladium catalyst removed by filtration and the $CHCl_3$ evaporated in vacuo. The redisue is distilled through a Vigreaux column to give about 1.83 g of 1-methylpyrrole-2-acetonitrile as a colorless oil, b.p. 68°–69°C at 0.3 mm/Hg.

EXAMPLE IV

Ethyl 1-Methylpyrrole-2-acetate

A mixture of 5.0 g of diethyl 1-methyl-Δ-2,α-pyrrolidinemalonate [see H. Bredereck et al., Ber. 94, 2278 (1961)], 1 g of 10% palladium on carbon and 15 ml of ethyl oleate is heated at 200°C for 18 hours under nitrogen. The mixture is then dissolved in $CHCl_3$, the palladium catalyst removed by filtration and the $CHCl_3$ evaporated in vacuo. The residue is distilled through a Vigreaux column. The first fraction, b.p. 47°–55°C at 0.05 mm/Hg comprises the product, ethyl 1-methylpyrrole-2-acetate of about 97% purity, as a yellow oil.

EXAMPLE V

Methyl α-cyano-1-methyl-Δ-2,α-pyrrolideneacetate

A solution of 28 g (0.284 mole) of phosgene in 80 ml of benzene is added to a solution of 28 g (0.284 mole) of 1-methyl-2-pyrrolidinone in 70 ml of benzene. The mixture is stirred for 3 hours at room temperature. The mixture is then cooled in an ice bath and 28.0 g (0.280 mole) of methyl cyanoacetate is added dropwise. Next, 56 g (0.56 mole) of triethylamine is added dropwise. The cooling bath is removed and the mixture is stirred for 2 hours in a water bath maintained at 50°–60°C. The mixture is then poured into water and extracted into benzene. The organic layer is separated, dried (over anhydrous $MgSO_4$) and evaporated to dryness in vacuo. The residue crystallizes and is recrystallized from 95% ethanol. Two crops of crystals of methyl-Δ-2,α-pyrrolideneacetate are obtained totaling about 17 g, m.p., 109°–110°C.

EXAMPLE VI

N-Methylpyrrole-2-acetic acid

A mixture of 2.0 g of methyl α-cyano-1-methyl-Δ-2,α-pyrrolideneacetate and 10 g of 10% palladium on carbon in 20 ml of p-cymene is heated slowly to reflux while ethylene is bubbled in. The flow of ethylene is shut off and the mixture heated under reflux for 18 hours. The mixture is then dissolved in $CHCl_3$, the palladium catalyst removed by filtration and the CHCl₃ evaporated in vacuo to give a solution of methyl 1-methylpyrrole-2-acetate and 1-methylpyrrole-2-acetonitrile in p-cymene. This solution is mixed with a solution of 1.2 g of sodium hydroxide in 20 ml of 95% ethanol and the mixture heated at 50°C for 1 hour. The mixture is then poured into water and the aqueous layer is separated and washed twice with ether, made acidic with dilute HCl and extracted with ether. The ether extract is washed with brine, dried over anhydrous MgSO₄ ane evaporated in vacuo to give about 0.7 g of a brown oil which crystallizes on trituration from hexane. The product is recrystallized twice from ether-hexane to give white crystals of 1-methylpyrrole-2-acetic acid, m.p. 97°–100°C.

EXAMPLE VII

A. N-Methylpyrrole-2-acetic acid is also obtained by repeating the procedure of Example VI except that an equivalent quantity of the ethyl ester of α-cyano-1-methyl-Δ-2,α-pyrrolidene acetate [see H. Bredereck et al., Ber. 94, 2278 (1961)] is used in place of the methyl ester used therein.

B. Ethyl N-methylpyrrole-2-acetate: Lower alkyl esters of N-methylpyrrole-2-acetic acid are prepared by conventional esterification techniques using an appropriate lower alkanol. For example, a solution of 0.028 mole of N-methylpyrrole-2-acetic acid in 50 ml of 0.5% ethanolic HCl is refluxed for 90 minutes. The solution is charcoaled, filtered and the filtrate evaporated in vacuo to yield the ester product, ethyl N-methylpyrrole-2-acetate.

EXAMPLE VIII

4-Methylpyrrolidene-2-thione

A mixture of 19.7 g of 4-methyl-2-pyrrolidinone and 9.0 g of phosphorous pentasulfide in 80 ml of xylene is heated under reflux for 2 hours. The mixture is filtered while hot. The solvent is evaporated in vacuo and the crystalline redisue recrystallized twice from acetone to give about 7.3 g of crystalline 4-methylpyrrolidene-2-thione, m.p. 93°–93.5°C.

EXAMPLE IX

Diethyl 4-methyl-Δ-2,α-pyrrolidenemalonate

A mixture of 11.45 g of 4-methylpyrrolidene-2-thione and 2.76 g of diethyl bromomalonate in 100 ml of CH₂Cl₂ is allowed to stand for 48 hours. The mixture is then diluted with 400 ml of CH₂Cl₂, the resultant solution washed with saturated KHCO₃ solution, dried (Na₂SO₄) and evaporated in vacuo. The residue is heated at 60°C for 2 hours and then dissolved in ether and filtered to remove elemental sulfur. The ether is evaporated in vacuo and the residue dissolved in ethanol and stirred for 1 hour with 4 teaspoons of Raney nickel to complete the removal of sulfur. The ethanol is evaporated in vacuo and the residue distilled in vacuo. There are obtained about 13.3 g of diethyl 4-methyl-Δ-2,α-pyrrolidenemalonate as a yellow oil, b.p. 144°–146°C (0.7mm/Hg).

EXAMPLE X

Ethyl 4-methylpyrrole-2-acetate 10.0 g Diethyl 4-methyl-Δ-2,α-pyrrolidenemalonate dissolved in 30 ml ethyl oleate is mixed with 3.3 g 10% Pd/C. The reaction mixture is stirred and heated overnight (about 16 hours) in a nitrogen atmosphere at 190°–210°C. The mixture is then cooled and filtered from catalyst which is washed with chloroform into the filtrate. The filtrate is evaporated in vacuo to give about 33 g brown oil which is distilled on a spinning band column. 1.0 Gram of a yellowish oil boiling at 90°–103°C/25mm is collected, dissolved in ether and washed in turn with 3N, HCl, saturated NaHCO₃ solution and brine, and then dried with Na₂SO₄. It is then evaporated to give about 0.3 g of a brown oil which is shown by gas liquid chromatography to contain 55% ethyl 4-methylpyrrole-2-acetate (2.4 % yield).

EXAMPLE XI

1-Methylpyrrole-2-acetonitrile

A solution of 1.0 g of methyl α-cyano-1-methyl-Δ2,α-pyrrolideneacetate in 60 ml of benzene is placed in a suitable pressure vessel with 0.5 g of 5% rhodium-on-alumina catalyst. After flushing with carbon dioxide, the mixture is heated at 250°C for 20 hours. The catalyst is removed by filtration. The filtrate is washed with dilute HCl followed by NaHCO₃ solution and then dried. The solvent is evaporated and the oily residue is shown by infrared spectroscopy and thin layer chromatography to contain 1-methylpyrrole-2-acetonitrile.

EXAMPLE XII

The procedure of Example XI is repeated except that an equivalent catalytic amount of platinum black is used instead of the rhodium-on-alumina to yield the product, 1-methylpyrrole-2-acetonitrile.

I claim:

1. The method which comprises catalytically dehydrogenating at 150°–450°C in a suitable inert organic solvent a pyrroldenemalonic acid derivative of the formula:

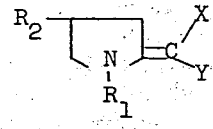

to yield the following products:

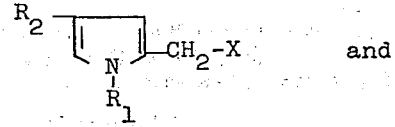      and

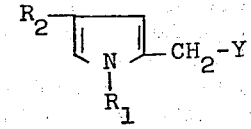

Wherein R₁ is a member selected from the group consisting of hydrogen and loweralkyl, R₂ is a member selected from the group consisting of hydrogen and methyl, and X and Y are each a member selected from the group consisting of COO(loweralkyl) and CN, and the dehydrogenation catalyst is a member selected from the group consisting of metallic palladium, platinum and rhodium.

2. The method of making a pyrroleacetonitrile of the formula:

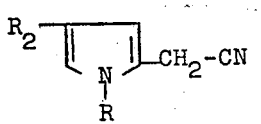

which comprises the catalytic dehydrogenation at 150°–450°C in a suitable inert organic solvent of a pyrrolidenemalonic acid di-nitrile of the formula:

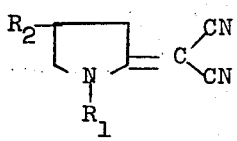

wherein $R_1$ is a member selected from the group consisting of hydrogen and loweralkyl, and $R_2$ is a member selected from the group consisting of hydrogen and methyl, and the dehydrogenation catalyst is a member selected from the group consisting of metallic palladium, platinum and rhodium.

3. The method of making a pyrrole-2-acetate of the formula:

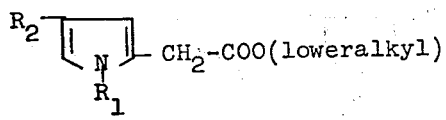

which comprises the catalytic dehydrogenation at 150°–450°C in a suitable inert organic solvent of a pyrrolidenemalonic acid di-ester of the formula:

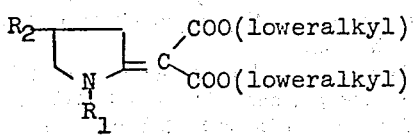

wherein $R_1$ is a member selected from the group consisting of hydrogen and loweralkyl, and $R_2$ is a member selected from the group consisting of hydrogen and methyl, and the dehydrogenation catalyst is a member selected from the group consisting of metallic palladium, platinum and rhodium.

4. The method of claim 1 wherein said $R_1$ is methyl and said $R_2$ is hydrogen.

5. The method of claim 2 wherein said $R_1$ is methyl and said $R_2$ is hydrogen.

6. The method of claim 3 wherein said $R_1$ and said $R_2$ are each hydrogen, and said loweralkyl is methyl.

7. The method of claim 3 wherein said $R_1$ is methyl, said $R_2$ is hydrogen and said loweralkyl is ethyl.

8. The method of claim 3 wherein said $R_1$ is hydrogen, said $R_2$ is methyl and said loweralkyl is ethyl.

9. The process of making a pyrrole-2-acetic acid of the formula:

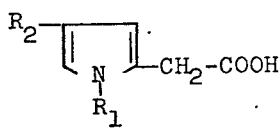

which comprises catalytically dehydrogenating at 150°–450°C in a suitable inert organic solvent a pyrrolidenemalonic acid derivative of the formula:

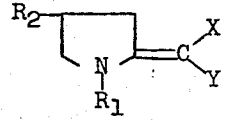

and subsequently hydrolyzing the thus-obtained dehydrogenated products of the formula:

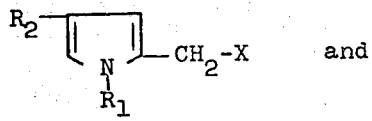   and

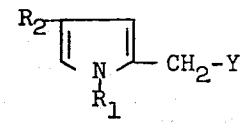

to yield the aforementioned pyrrole-2-acetic acid; wherein $R_1$ and $R_2$ are each a member selected from the group consisting of hydrogen and loweralkyl, and X and Y are each a member selected from the group consisting of COO(lower-alkyl) and CN, and the dehydrogenation catalyst is a member selected from the group consisting of metallic palladium, platinum and rhodium.

10. The process of making a pyrrole-2-acetic acid of the formula:

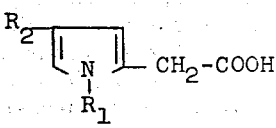

which comprises catalytically dehydrogenating at 150°–450°C in a suitable inert organic solvent a pyrrolidenemalonic acid di-nitrile of the formula:

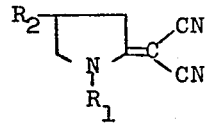

and subsequently hydrolyzing the thus-obtained pyrrole-2-acetonitrile of the formula:

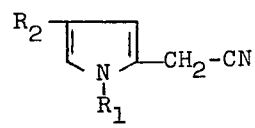

utilizing nitrile-to-acid hydrolysis conditions to yield the aforementioned pyrrole-2-acetic acid; wherein $R_1$ and $R_2$ are each a member selected from the group consisting of hydrogen and loweralkyl, and the dehydrogenation catalyst is a member selected from the group consisting of metallic palladium, platinum and rhodium.

11. The process of claim 2 wherein said $R_1$ is methyl and said $R_2$ is hydrogen.

12. The process of making a pyrrole-2-acetic acid of the formula:

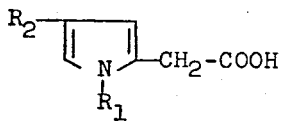

which comprises catalytically dehydrogenating at 150°–450°C in a suitable inert organic solvent a pyrrolidenemalonic acid di-ester of the formula:

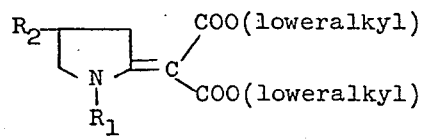

and subsequently hydrolyzing the thus-obtained pyrrole-2-acetate of the formula:

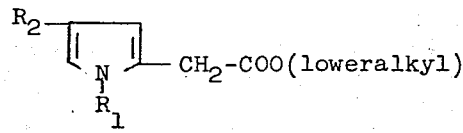

utilizing ester-to-nitrile hydrolysis conditions to yield the desired pyrrole-2-acetic acid; wherein $R_1$ and $R_2$ are each a member selected from the group consisting of hydrogen and loweralkyl, and the dehydrogenation catalyst is a member selected from the group consisting of metallic palladium, platinum and rhodium.

13. The process of claim 4 wherein said $R_1$ and said $R_2$ are each hydrogen, and said loweralkyl is methyl.

14. The process of claim 4 wherein said $R_1$ is methyl, said $R_2$ is hydrogen and said loweralkyl is ethyl.

15. The process of claim 4 wherein said $R_1$ is hydrogen, said $R_2$ is methyl and said loweralkyl is ethyl.

16. The process of making a pyrrole-2-acetic acid of the formula:

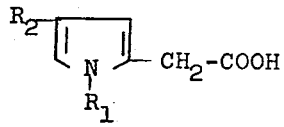

which comprises catalytically dehydrogenating at 150°–450°C in a suitable inert organic solvent a pyrrolidenemalonic acid mixed nitrile-ester of the formula:

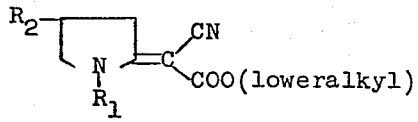

and subsequently hydrolyzing the thus-obtained dehydrogenated products of the formula:

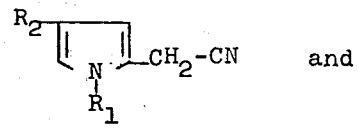 and

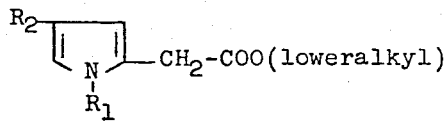

to yield the aforementioned pyrrole-2-acetic acid; wherein $R_1$ and $R_2$ are each a member selected from the group consisting of hydrogen and loweralkyl, and the dehydrogenation catalyst is a member selected from the group consisting of palladium, metallic platinum and rhodium.

17. The process of claim 8 wherein said $R_1$ is methyl said $R_2$ is hydrogen and said loweralkyl is methyl.

18. The process of claim 8 wherein said $R_1$ is methyl, said $R_2$ is hydrogen and said loweralkyl is ethyl.

* * * * *

UNITED STATES PATENT OFFICE
CERTIFICATE OF CORRECTION

Patent No. 3,957,818         Dated May 18, 1976

Inventor(s) John Robert Carson

It is certified that error appears in the above-identified patent and that said Letters Patent are hereby corrected as shown below:

Column 3, line 39, "10800e" should read -- 10880e --.

Column 12, line 40, "palladium, metallic" should read -- metallic palladium --.

Signed and Sealed this

First Day of November 1977

[SEAL]

Attest:

RUTH C. MASON
Attesting Officer

LUTRELLE F. PARKER
Acting Commissioner of Patents and Trademarks